(12) United States Patent  (10) Patent No.: US 8,394,073 B1
Williams  (45) Date of Patent: Mar. 12, 2013

(54) MALE CATHETER AND PUMP SYSTEM AND ASSOCIATED METHOD

(76) Inventor: Leroy H. Williams, Glenside, PA (US)

(*) Notice: Subject to any disclaimer, the term of this patent is extended or adjusted under 35 U.S.C. 154(b) by 681 days.

(21) Appl. No.: 12/567,745

(22) Filed: Sep. 26, 2009

Related U.S. Application Data

(60) Provisional application No. 61/194,386, filed on Sep. 26, 2008.

(51) Int. Cl.
*A61F 5/44* (2006.01)
(52) U.S. Cl. .......................... 604/319; 604/349
(58) Field of Classification Search .......... 604/319, 604/320, 323, 327–329, 349, 544
See application file for complete search history.

(56) References Cited

U.S. PATENT DOCUMENTS

| 4,994,051 | A | | 2/1991 | Walsh | |
|---|---|---|---|---|---|
| 5,002,541 | A | * | 3/1991 | Conkling et al. | 604/319 |
| D357,979 | S | | 5/1995 | Evans | |
| 7,160,276 | B2 | | 1/2007 | Bruns | |
| 7,186,245 | B1 | | 3/2007 | Cheng | |
| 2007/0010797 | A1 | * | 1/2007 | Nishtala et al. | 604/540 |

* cited by examiner

*Primary Examiner* — Melanie Hand

(57) ABSTRACT

A male catheter and pump system includes an external catheter, a temporary collection reservoir, and a water pump. The invention may further include a user interface, a controller and a pump to drain excess urine for the temporary collection reservoir. An inlet spout located on the external catheter may be adapted to receive the waste fluid from a user such as a bedridden patient. A first tube is connected from the external catheter to the temporary collection reservoir and a second tube is further connected from the temporary collection reservoir to a dispensing reservoir for permanent disposal of the urine. A sensor and a one-way valve are located in the temporary collection reservoir where the controller automatically transmits signals to operate the water pump and open the one-way valve to dispose the urine into the dispensing reservoir.

7 Claims, 5 Drawing Sheets

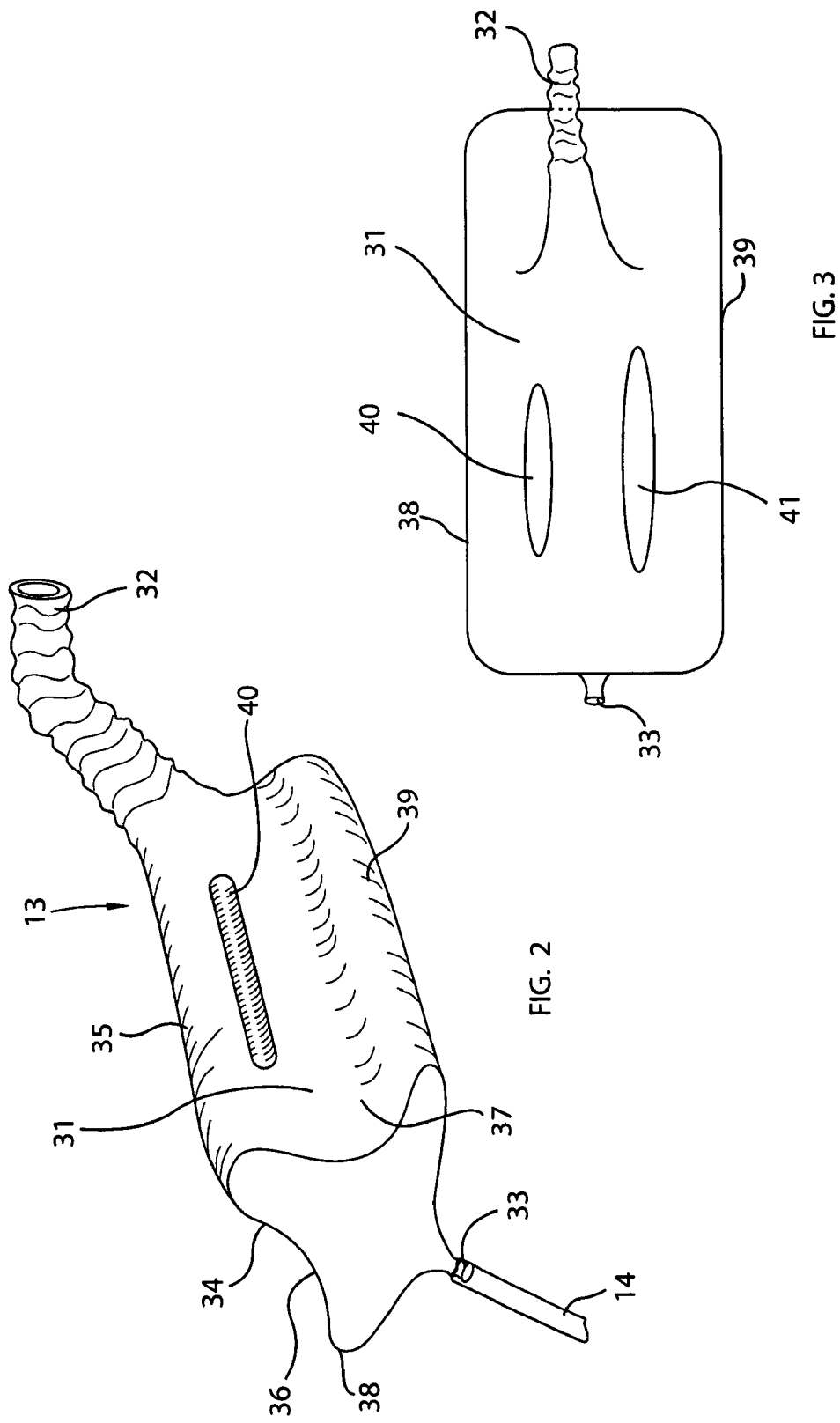

MALE CATHETER AND PUMP SYSTEM AND ASSOCIATED METHOD

CROSS REFERENCE TO RELATED APPLICATIONS

This application claims the benefit of U.S. Provisional Application No. 61/194,386, filed Sep. 26, 2008, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to urine collection bins and, more particularly, to a catheter and pump system and associated method for providing bedridden male users with a comfortable and effective means of passing bodily waste without having to get out of bed.

2. Prior Art

Over 54 million Americans suffer from some form of limited mobility. In fact, according to statistics complied by the Center for Disease Control (CDC), these numbers are ever increasing. Limited mobility can result from a variety of causes such as arthritis, muscle deterioration or inactivity. The most common reason people suffer limited mobility; however, is a result of falls. This is particularly prevalent in the older population where problems with balance, musculoskeletal disabilities, medication use and visual impairment can all cause a person to easily lose their step. In addition to limited mobility, countless consumers suffer from infirmities which can render them bedridden.

Whether one is braving a debilitating terminal illness, or simply enduring a temporary period of recovery after invasive surgery, the inability to freely move about can render even the simplest of tasks difficult. Specifically, the simple act of using the rest room can be extremely daunting for one who is bedridden or suffers limited mobility. This problem can be especially taxing during the evening hours, or when one is left alone and unassisted. For those with serious medical conditions, using the bathroom on their own is simply not an option. Unfortunately, these consumers must wait patiently for help to arrive, or must utilize adult incontinence products for relief, Resulting in a loss if independence, as well as discomfort and embarrassment, the problem of needing assistance simply in order to use the rest room is one most consumers would rather do without.

Accordingly, a need remains for a male catheter and pump system in order to overcome the above-noted shortcomings. The present invention satisfies such a need by providing a male catheter and pump system that is convenient and easy to use lightweight yet durable in design and designed for providing bedridden male users with a means to convenient and comfortable means of passing human waste without having to get out of bed.

BRIEF SUMMARY OF THE INVENTION

In view of the foregoing background, it is therefore an object of the present invention to provide a combined male catheter and pump system transports body fluid waste away from a bedridden patient and preferably includes a user interface for generating first and second input signals upon receiving first and second user inputs. A controller may be communicatively coupled to the user interface such that the controller may generate first and second pump control signals upon receiving the first and second input signals from the user interface.

The present invention may further include an external catheter having a proximal end adapted to receive the body fluid waste directly from a patient. A first tube preferably has a proximal end connected to a distal end of the external catheter and is in fluid communication therewith. A water pump is preferably located downstream of the external catheter and a temporary collection reservoir may be removably connected to the first tube such that the temporary collection reservoir is in fluid communication with the water pump. In this manner, the water pump may be toggled between active and inactive modes upon receiving the first and second pump control signals for directing the body fluid waste along a downstream path leading away from the external catheter.

In one embodiment, the present invention may further include a second tube preferably having a proximal end connected to the temporary collection reservoir such that the second tube is in selective fluid communication with the temporary collection reservoir. A dispensing reservoir may be in fluid communication with a distal end of the second tube.

In one embodiment, a sensor may be situated within the temporary collection reservoir for generating and transmitting first and second signals to the controller when a real-time fluid level in the temporary collection reservoir is above and below a maximum threshold fluid level. A one-way valve may be situated at the proximal end of the second tube and located exterior of the temporary collection reservoir. In this manner, the controller may generate and transmit first and second valve control signals to the one-way valve and thereby automatically toggles the one-way valve between open and closed positions for permitting and prohibiting the body fluid waste to egress the temporary collection reservoir respectively.

In one embodiment, the temporary collection reservoir may further include an inlet in fluid communication with the first tube. In this manner, the water pump may be located downstream of the inlet while situated at the temporary collection reservoir. The temporary collection reservoir may further include an outlet in fluid communication with the second tube. Advantageously, the one-way valve may be located downstream of the outlet while situated within the second tube.

In one embodiment, the external catheter may include a central holding chamber adapted to receive the body fluid waste and a deformable inlet spout attached to a proximal end of the holding chamber. The inlet spout may be in fluid communication with the central holding chamber. An outlet spout is attached to the distal end of the cavity and may further be in fluid communication with the proximal end of the first tube.

In one embodiment, the central holding chamber may include an outer surface preferably having a linear apex centrally aligned with a longitudinal length of the inlet spout. The outer surface further having a pair of oppositely situated shoulders flanging downwardly and laterally away from the apex. Such shoulders may be equidistantly offset from the apex and thereby terminate at left and right longitudinal sides of the holding chamber.

The present invention may further include a method of utilizing a combined male catheter and pump system for transporting body fluid waste away from a bedridden patient.

The method preferably includes the chronological steps of: providing a user interface; the user interface generating first and second input signals upon receiving first and second user inputs; providing and communicatively coupling a controller to the user interface; and the controller generating first and second pump control signals upon receiving the first and second input signals from the user interface respectively.

The method may further include the chronological steps of: providing and positioning an external catheter on a urinary discharge organ of the patient; the external catheter having a proximal end receiving the body fluid waste directly from the patient; and providing and connecting a proximal end of a first tube to a distal end of the external catheter so that the first tube is in fluid communication with the external catheter.

The method may further include the chronological steps of: providing and locating a water pump downstream of the external catheter; providing and removably connecting a temporary collection reservoir to the first tube such that the temporary collection tubing is in fluid communication with the water pump; and directing the body fluid waste along a downstream path leading away from the external catheter by toggling the water pump between active and inactive modes upon receiving the first and second pump control signals respectively.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

FIG. 2 is a perspective view of the external catheter;

FIG. 3 is a top plan view of the external catheter;

Figure 1:
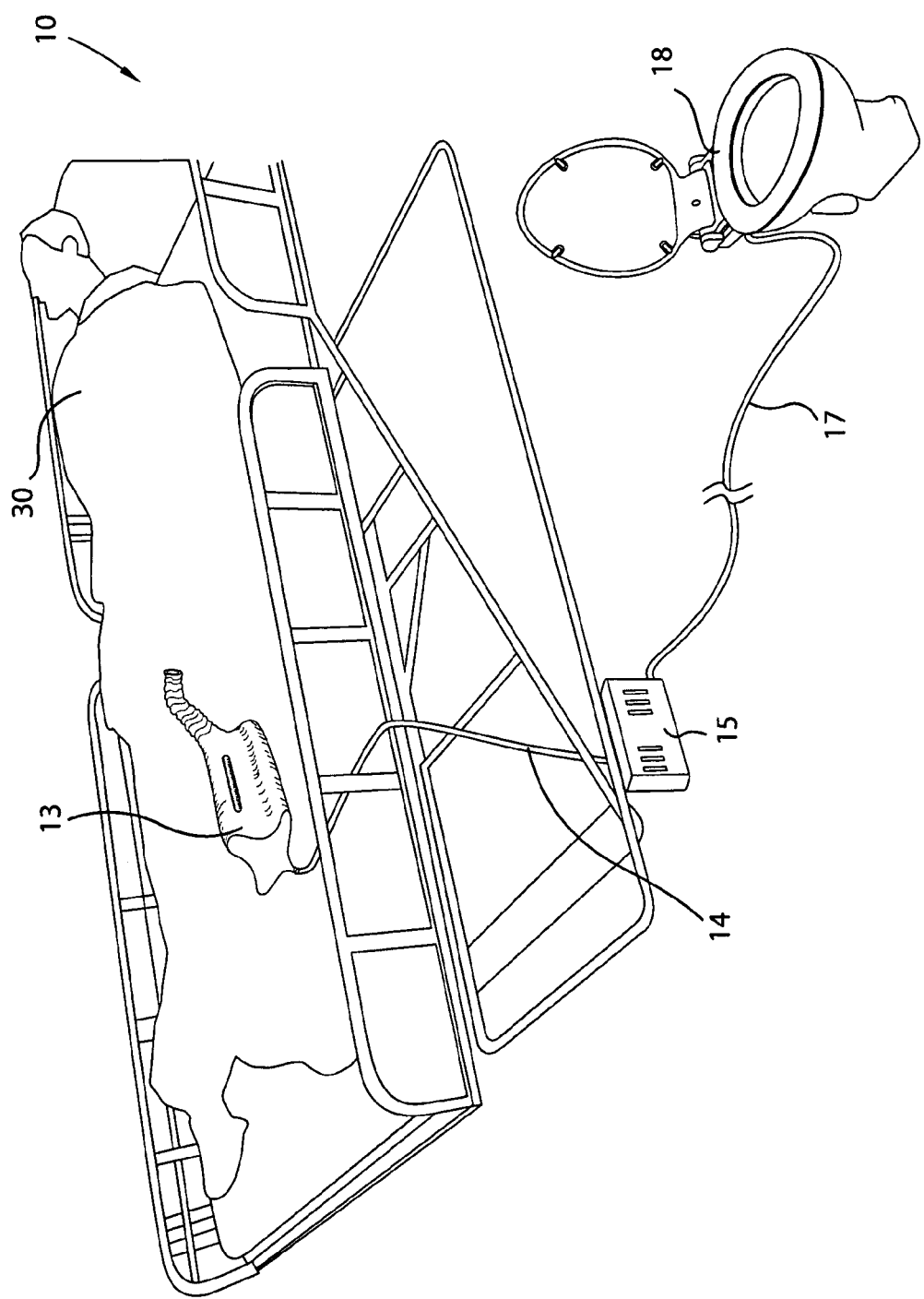
FIG. 1 is a perspective view showing a catheter and pump system, in accordance with the present invention.
Figure 4:
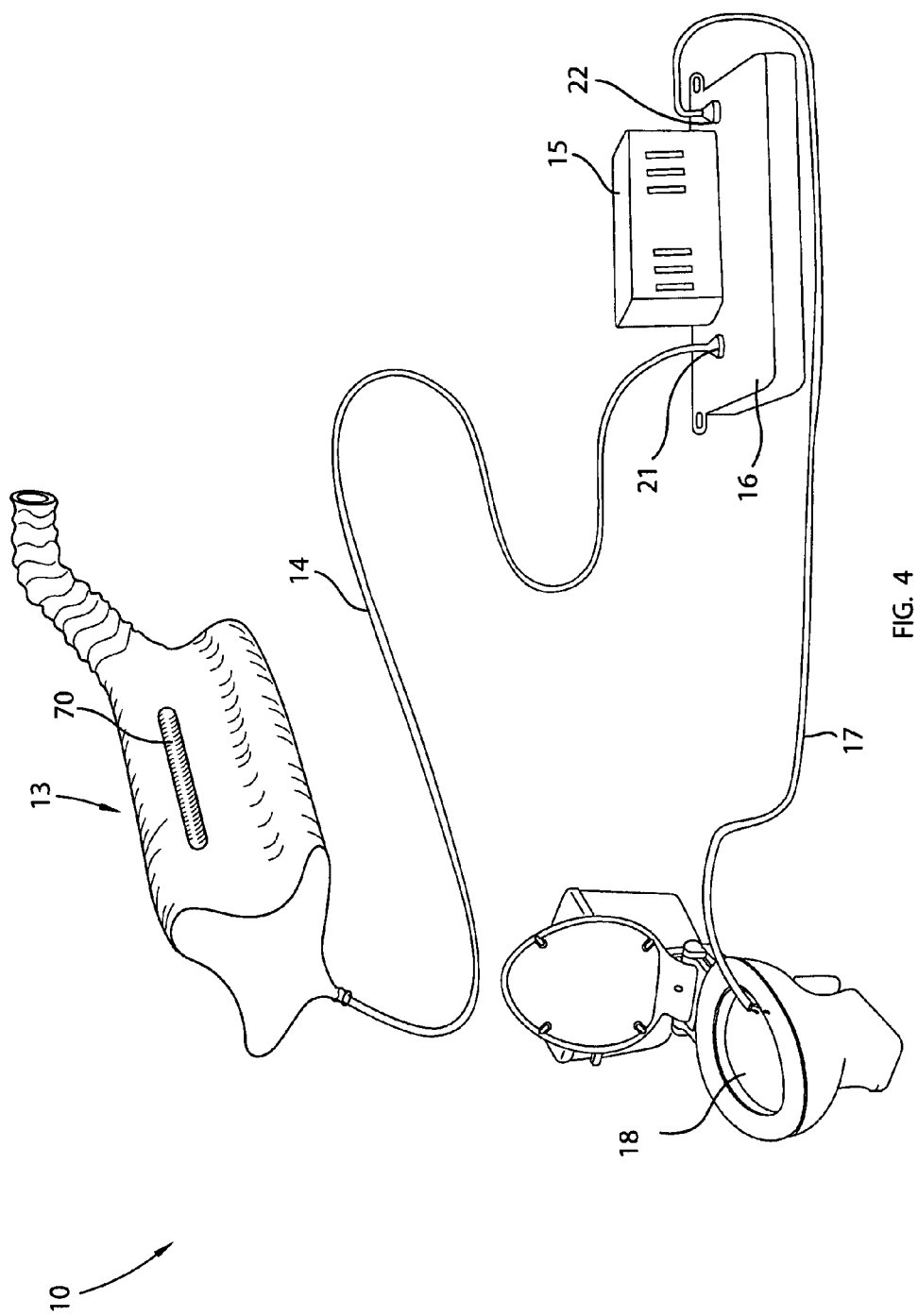
FIG. 4 is perspective view showing the interrelationship between the external catheter, first and second tubes, temporary collection reservoir, water pump and disposal reservoir, in accordance with one embodiment of the present invention.

Those skilled in the art will appreciate that the figures are not intended to be drawn to any particular scale; nor are the figures intended to illustrate every embodiment of the invention. The invention is not limited to the exemplary embodiments depicted in the figures or the shapes, relative sizes or proportions shown in the figures.

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The system of this invention is referred to generally in FIGS. 1-6 by the reference numeral 10 and is intended to provide a combined external catheter and pump system. It should be understood that the present invention may be used to extract and collect urine from many different types of bedridden user and should not be limited to only bedridden users in a hospital.

A combined male catheter and pump system 10 transports body fluid waste away from a bedridden patient 30 and preferably includes a user interface 11 for generating first and second input signals upon receiving first and second user inputs. A controller 12 may be communicatively coupled to the user interface 11 such that the controller 12 may generate first and second pump control signals upon receiving the first and second input signals from the user interface 11. Such claimed elements provide the advantage of allowing a user to actively control the discharge of urine that is collected after release and thereby solves the problem of urine overflow and backup within the tubing. Such a combination of claimed elements provides an unpredictable and unexpected result which is not rendered obvious by one skilled in the art.

The present invention may further include an external catheter 13 having a proximal end adapted to receive the body fluid waste directly from patient 30. A first tube 14 preferably has a proximal end connected to a distal end of the external catheter 13 and is in fluid communication therewith. A water pump 15 is preferably located downstream of the external catheter 13 and a temporary collection reservoir 16 may be removably connected to the first tube 14 such that the temporary collection reservoir 16 is in fluid communication with the water pump 15. In this manner, the water pump 15 may be toggled between active and inactive modes upon receiving the first and second pump control signals for directing the body fluid waste along a downstream path leading away from the external catheter 13. Such claimed elements provide the advantage of temporarily pumping and storing the released urine and thereby solving the problem of inadequate urine drainage and disposal during extended periods of time. Such a combination of claimed elements provides an unpredictable and unexpected result which is not rendered obvious by one skilled in the art.

In one embodiment, the present invention may further include a second tube 17 preferably having a proximal end connected to the temporary collection reservoir 16 such that the second tube 17 is in selective fluid communication with the temporary collection reservoir 16. A dispensing reservoir 18 may be in fluid communication with a distal end of the second tube 17. Such claimed elements provide the advantage of dispensing the collected urine from the temporary collection reservoir 16 and thereby solving the problem of having to repeatedly empty the temporary collection reservoir 16 during extended time periods. Such a combination of claimed elements provides an unpredictable and unexpected result which is not rendered obvious by one skilled in the art.

In one embodiment, a sensor 19 may be situated within the temporary collection reservoir 16 for generating and transmitting first and second signals to the controller 12 when a real-time fluid level in the temporary collection reservoir 16 is above and below a maximum threshold fluid level. Such a maximum threshold fluid level may be predetermined by the caregiver based upon the location of the sensor 19 within the temporary collection reservoir 16. A one-way valve 20 may be situated at the proximal end of the second tube 17 and located exterior of the temporary collection reservoir 16. In this manner, in response to receiving the first and second signals from the sensor 19, the controller 12 may generate and transmit first and second valve control signals to the one-way valve 20 and thereby automatically toggle the one-way valve 20 between open and closed positions for permitting and prohibiting the body fluid waste to egress the temporary collection reservoir 16 respectively. Such claimed elements provide the advantage of automatically emptying the temporary collection reservoir 16 when it is full and thereby solves the problem of undesirable urine overflow from the temporary collection reservoir. Such a combination of claimed elements provides an unpredictable and unexpected result which is not rendered obvious by one skilled in the art.

Figure 6:
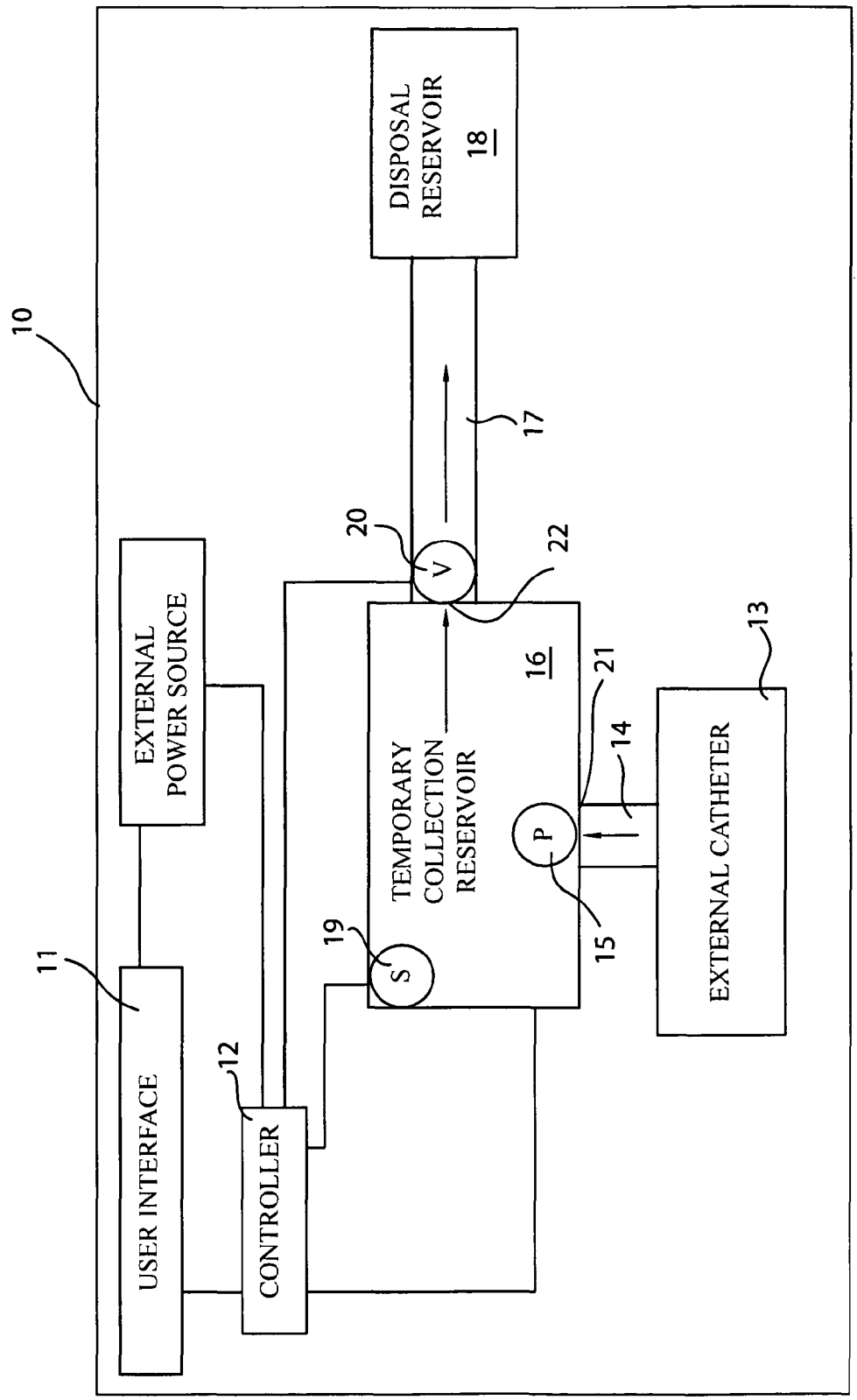
FIG. 6 is a high-level schematic block diagram showing the interrelationship between the major components of the present invention wherein a flow path of the body fluid waste as it passes through the temporary collection reservoir.

As perhaps best shown in FIGS. 2, 3 and 6, the temporary collection reservoir 16 may further include an inlet 21 in fluid communication with the first tube 14. In this manner, the water pump 15 may be located downstream of the inlet 21 while situated at the temporary collection reservoir 16. The temporary collection reservoir 16 may further include an outlet 22 in fluid communication with the second tube 17. Advantageously, the one-way valve 20 may be located downstream of the outlet 22 while situated within the second tube 17. Such claimed elements provide the advantage of ensuring that the urine does not flow back to the external catheter. This solves the problem of urine leakage on the user's bed due to limited space within the temporary collection reservoir 16. Such a combination of claimed elements provides an unpredictable and unexpected result which is not rendered obvious by one skilled in the art.

As perhaps best shown in FIGS. 2 and 3, the external catheter 13 may include a central holding chamber 31 adapted to receive the body fluid waste and a deformable inlet spout 32 attached to a proximal end of the holding chamber 31. The inlet spout 32 may be in fluid communication with the central holding chamber 31. An outlet spout 33 is attached to the distal end of the cavity and may further be in fluid communication with the proximal end of the first tube 14. Such claimed elements provide the advantage of detachably coupling the external catheter 13 from the first tube 14 during routine cleaning procedures and thereby solves the problem of urine contamination within the first tube 14 and holding chamber 31 during prolonged use. Such a combination of claimed elements provides an unpredictable and unexpected result which is not rendered obvious by one skilled in the art.

Figure 5:
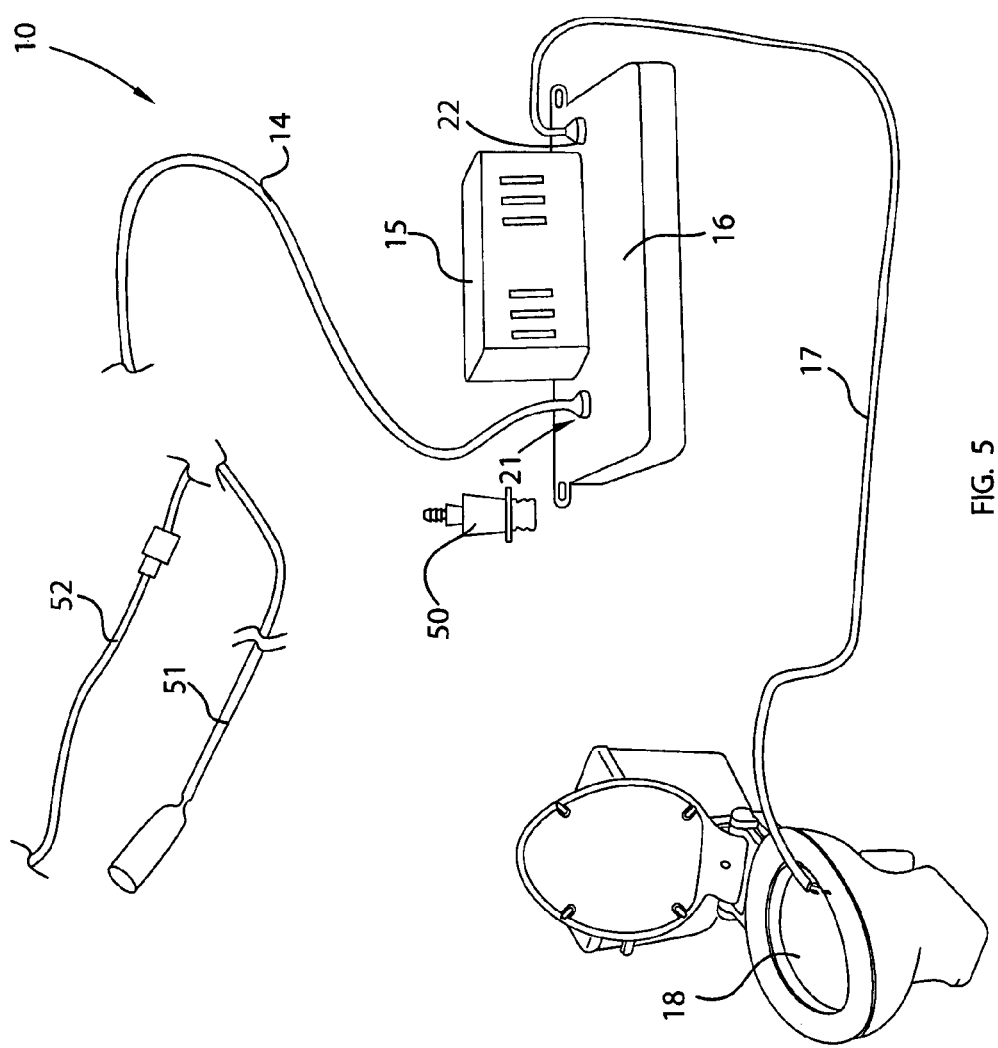
FIG. 5 is a perspective view showing the auxiliary male and female auxiliary extensions for the external catheter.

Referring to FIG. 5, auxiliary male and female catheter extensions 51, 52 may also be provided for being removably connected to the temporary collection reservoir 16 and the external catheter 13, as needed. Coupling 50 may also be employed to provide a secure connection between the distal end of the first tube 14 and the inlet 21 of the temporary collection reservoir 16. Such a coupling 50 may have a barb connector at one end and a threaded connector at an opposite end, for example.

In one embodiment, the central holding chamber 31 may include an outer surface 34 preferably having a linear apex 35 centrally aligned with a longitudinal length of the inlet spout 32. The outer surface 34 further has a pair of oppositely situated shoulders 36, 37 flanging downwardly and laterally away from the apex. Such shoulders 36, 37 may be equidistantly offset from the apex 35 and thereby terminate at left and right longitudinal sides 38, 39 of the central holding chamber 31, respectively. The central holding chamber 31 may further include a plurality of viewing windows 40, 41 located on the shoulders 36, 37 respectively. A handle 70 may also be provided for assisting caregiver to transport the external catheter 13 away from the patient. Such claimed elements provide the advantage of allowing a caregiver to check the external catheter 13 and thereafter determine whether to activate the water pump 15 to drain the urine from the central holding chamber 31. Such a benefit solves the problem of urine overflow and backup at the external catheter 13. Such a combination of claimed elements provides an unpredictable and unexpected result which is not rendered obvious by one skilled in the art.

The present invention may further include a method of utilizing a combined male catheter and pump system 10 for transporting body fluid waste away from a bedridden patient 30. The method preferably includes the chronological steps of: providing a user interface 11; the user interface 11 generating first and second input signals upon receiving first and second user inputs; providing and communicatively coupling a controller 12 to the user interface 11; and the controller 12 generating first and second pump control signals upon receiving the first and second input signals from the user interface 11, respectively. Such claimed elements provide the advantage of automatically transporting body fluid waste away from the bedridden patient 30 and thereby solves the problem of urine leakage in a patient's bed. Such a combination of claimed elements provides an unpredictable and unexpected result which is not rendered obvious by one skilled in the art.

The method may further include the chronological steps of: providing and positioning an external catheter 13 on a urinary discharge organ of the patient 30; the external catheter 13 having a proximal end receiving the body fluid waste directly from the patient; and providing and connecting a proximal end of a first tube 14 to a distal end of the external catheter 13 so that the first tube 14 is in fluid communication with the external catheter 13. Such claimed elements provide the advantage of directing the body fluid waste away from the patient after discharge and thereby solves the problem of urine leakage on a patient's bed. Such a combination of claimed elements provides an unpredictable and unexpected result which is not rendered obvious by one skilled in the art.

The method may further include the chronological steps of: providing and locating a water pump 15 downstream of the external catheter 13; providing and removably connecting a temporary collection reservoir 16 to the first tube 14 such that the temporary collection reservoir 16 is in fluid communication with the water pump 15; and directing the body fluid waste along a downstream path leading away from the external catheter 13 by toggling the water pump 15 between active and inactive modes upon receiving the first and second pump control signals respectively. Such claimed elements provide the advantage of periodically and hygienically removing the urine from the external catheter 13 and thereby solves the problem of having to perform extensive bed and medical equipment cleaning associated with bedridden patients. Such a combination of claimed elements provides an unpredictable and unexpected result which is not rendered obvious by one skilled in the art.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A combined male catheter and pump system for transporting body fluid waste away from a bedridden patient, said male catheter and pump system comprising:
   a user interface for generating first and second input signals upon receiving first and second user inputs;
   a controller communicatively coupled to said user interface, said controller generating first and second pump control signals upon receiving said first and second input signals from said user interface respectively;
   an external catheter having a proximal end adapted to receive the body fluid waste directly from the patient;
   a first tube having a proximal end connected to a distal end of said external catheter and being in fluid communication therewith;
   a water pump located downstream of said external catheter;
   a temporary collection reservoir connected to said first tube;
   wherein said water pump toggles between active and inactive modes upon receiving said first and second pump control signal for directing the body fluid waste along a downstream path leading away from said external catheter;
   a second tube having a proximal end connected to said temporary collection reservoir and being in selective fluid communication therewith;
   a dispensing reservoir in fluid communication with a distal end of said second tube;
   a sensor situated within said temporary collection reservoir, said sensor generating and transmitting first and second signals to said controller when a real-time fluid level in said temporary collection reservoir is above and below a maximum threshold fluid level respectively; and
   a one-way valve situated at said proximal end of said second tube and being located exterior of said temporary collection reservoir;
   wherein said controller generates and transmits first and second valve control signals to said one-way valve and thereby automatically toggles said one-way valve between open and closed positions for permitting and prohibiting the body fluid waste to egress said temporary collection reservoir respectively;
   wherein said temporary collection reservoir comprises
   an inlet in fluid communication with said first tube, said water pump being located downstream of said inlet while situated at said temporary collection reservoir; and
   an outlet in fluid communication with said second tube, said one-way valve being located downstream of said outlet while situated within said second tube.

2. The combined male catheter and pump system of claim 1, wherein said external catheter comprises:
   a central holding chamber adapted to receive the body fluid waste therein;
   a deformable inlet spout attached to a proximal end of said holding chamber and being in fluid communication therewith; and
   an outlet spout attached to said distal end of said cavity and being in fluid communication with said proximal end of said first tube.

3. The combined male catheter and pump system of claim 2, wherein said central holding chamber comprises: an outer surface having a linear apex centrally aligned with a longitudinal length of said inlet spout, said outer surface further having a pair of oppositely situated shoulders flanging downwardly and laterally away from said apex, said shoulders being equidistantly offset from said apex and terminating at left and right longitudinal sides of said holding chamber.

4. A combined male catheter and pump system for transporting body fluid waste away from a bedridden patient, said male catheter and pump system comprising:
   a user interface for generating first and second input signals upon receiving first and second user inputs;
   a controller communicatively coupled to said user interface, said controller generating first and second pump control signals upon receiving said first and second input signals from said user interface respectively;
   an external catheter having a proximal end adapted to receive the body fluid waste directly from the patient;
   a first tube having a proximal end connected to a distal end of said external catheter and being in fluid communication therewith;
   a water pump located downstream of said external catheter;
   a temporary collection reservoir removably connected to said first tube and being in fluid communication with said water pump;
   wherein said water pump toggles between active and inactive modes upon receiving said first and second pump control signal for directing the body fluid waste along a downstream path leading away from said external catheter;
   a second tube having a proximal end connected to said temporary collection reservoir and being in selective fluid communication therewith;
   a dispensing reservoir in fluid communication with a distal end of said second tube.
   a sensor situated within said temporary collection reservoir, said sensor generating and transmitting first and second signals to said controller when a real-time fluid level in said temporary collection reservoir is above and below a maximum threshold fluid level respectively;
   a one-way valve situated at said proximal end of said second tube and being located exterior of said temporary collection reservoir;
   wherein said controller generates and transmits first and second valve control signals to said one-way valve and thereby automatically toggles said one-way valve between open and closed positions for permitting and prohibiting the body fluid waste to egress said temporary collection reservoir respectively;
   wherein said temporary collection reservoir comprises:
   an inlet in fluid communication with said first tube, said water pump being located downstream of said inlet while situated at said temporary collection reservoir; and an outlet in fluid communication with said second tube, said one-way valve being located downstream of said outlet while situated within said second tube.

5. The combined male catheter and pump system of claim 4, wherein said external catheter comprises:
   a central holding chamber adapted to receive the body fluid waste therein;
   a deformable inlet spout attached to a proximal end of said holding chamber and being in fluid communication therewith; and
   an outlet spout attached to said distal end of said cavity and being in fluid communication with said proximal end of said first tube.

6. The combined male catheter and pump system of claim 5, wherein said central holding chamber comprises: an outer surface having a linear apex centrally aligned with a longitudinal length of said inlet spout, said outer surface further having a pair of oppositely situated shoulders flanging downwardly and laterally away from said apex, said shoulders being equidistantly offset from said apex and terminating at left and right longitudinal sides of said holding chamber.

7. A method of utilizing a combined male catheter and pump system for transporting body fluid waste away from a bedridden patient, said method comprising the chronological steps of:
   providing a user interface;
   said user interface generating first and second input signals upon receiving first and second user inputs;
   providing and communicatively coupling a controller to said user interface;
   said controller generating first and second pump control signals upon receiving said first and second input signals from said user interface respectively;
   providing and positioning an external catheter on a urinary discharge organ of the patient;
   said external catheter having a proximal end receiving the body fluid waste directly from the patient;
   providing and connecting a proximal end of a first tube to a distal end of said external catheter so that said first tube is in fluid communication with said external catheter;
   providing and locating a water pump downstream of said external catheter;
   providing and removably connecting a temporary collection reservoir to said first tube such that said temporary collection reservoir is in fluid communication with said water pump; and
   directing the body fluid waste along a downstream path leading away from said external catheter by toggling said water pump between active and inactive modes upon receiving said first and second pump control signals respectively.

\* \* \* \* \*